United States Patent [19]

Miodownik

[11] Patent Number: 4,570,639

[45] Date of Patent: Feb. 18, 1986

[54] DISCONTINUITY DETECTOR

[75] Inventor: Saul Miodownik, Bronx, N.Y.

[73] Assignee: Memorial Hospital for Cancer and Allied Diseases, New York, N.Y.

[21] Appl. No.: 454,523

[22] Filed: Dec. 30, 1982

[51] Int. Cl.$^4$ .............................................. A61B 5/08
[52] U.S. Cl. ................................... 128/718; 604/65; 73/861.41; 340/608; 422/83
[58] Field of Search .................................. 604/65–67, 604/245, 253, 118; 128/DIG. 13, 718–719, 730; 73/861.41; 340/608–609, 600, 619; 422/83–84; 364/415–416

[56] References Cited

U.S. PATENT DOCUMENTS

| | | | |
|---|---|---|---|
| 2,967,450 | 1/1961 | Shields et al. | 73/861.41 X |
| 3,000,377 | 9/1961 | Tolbert et al. | 128/718 |
| 3,197,068 | 7/1965 | Corbin et al. | 604/65 X |
| 3,257,782 | 6/1966 | Weiss | 55/215 |
| 3,339,578 | 9/1967 | Smith | 137/392 |
| 3,395,699 | 8/1968 | Beasley | 128/728 |
| 3,450,153 | 6/1969 | Hildebrandt et al. | 604/65 X |
| 3,648,694 | 3/1972 | Mogos et al. | 128/DIG. 13 X |
| 3,890,968 | 6/1975 | Pierce et al. | 604/65 |
| 4,197,858 | 4/1980 | Osborn | 128/718 |
| 4,312,341 | 1/1982 | Zissnopoulos et al. | 604/67 |
| 4,314,484 | 2/1982 | Bowman | 604/65 X |
| 4,367,736 | 1/1983 | Gupton | 604/67 |

Primary Examiner—Lee S. Cohen
Assistant Examiner—Angela D. Sykes
Attorney, Agent, or Firm—Felfe & Lynch

[57] ABSTRACT

A discontinuity detector detects a sudden change or discontinuity in a medium moving relative to the detector such as a liquid plug in a gas flowing along a conduct, an air bubble in a liquid, or a change form one liquid or gas to another. It has a sensor which senses the discontinuity and a circuit which compensates for gradual changes in the medium or sensor, but responds to the sensed discontinuity. The preferred circuit also determines that the sensor is functioning properly and is properly set up for sensing the discontinuity. The preferred circuit is an analog-to-digital delta modulator which periodically resets a clock pulse counter until a discontinuity is sensed. The clock pulses then increment the counter to a higher-than-normal count to signal the discontinuity. The preferred embodiments are intended for detecting discontinuities in patient gas or liquid supplies in a medical diagnostic or therapeutic instrument.

14 Claims, 3 Drawing Figures

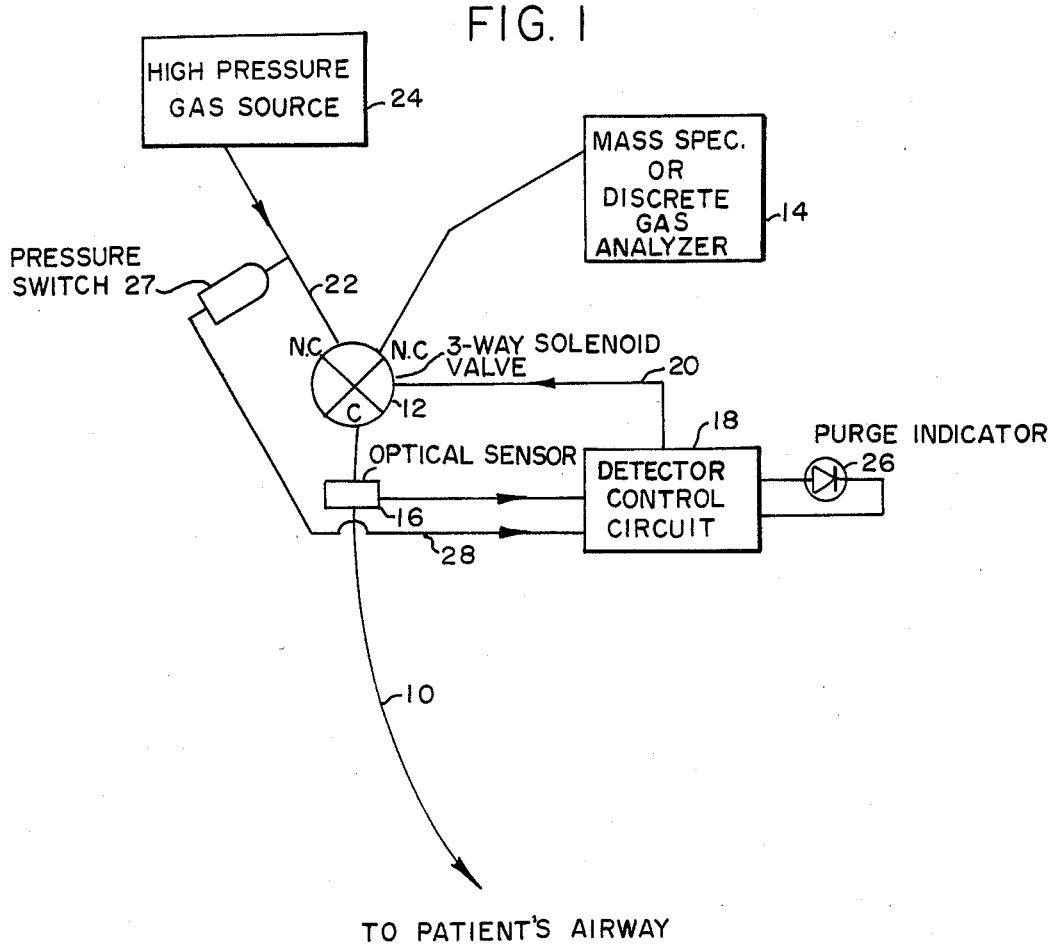
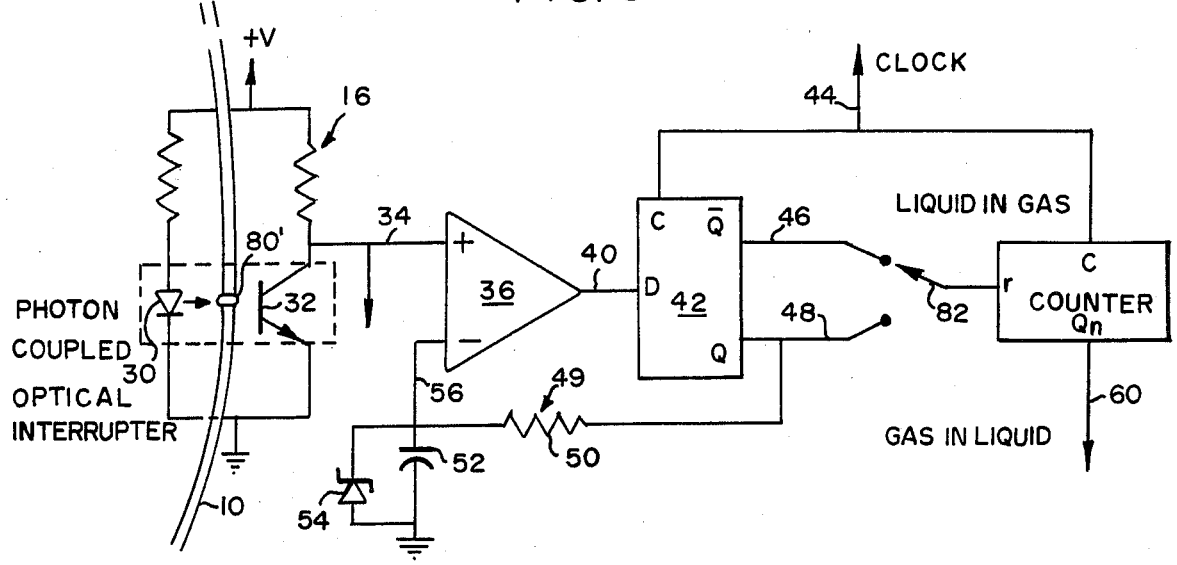

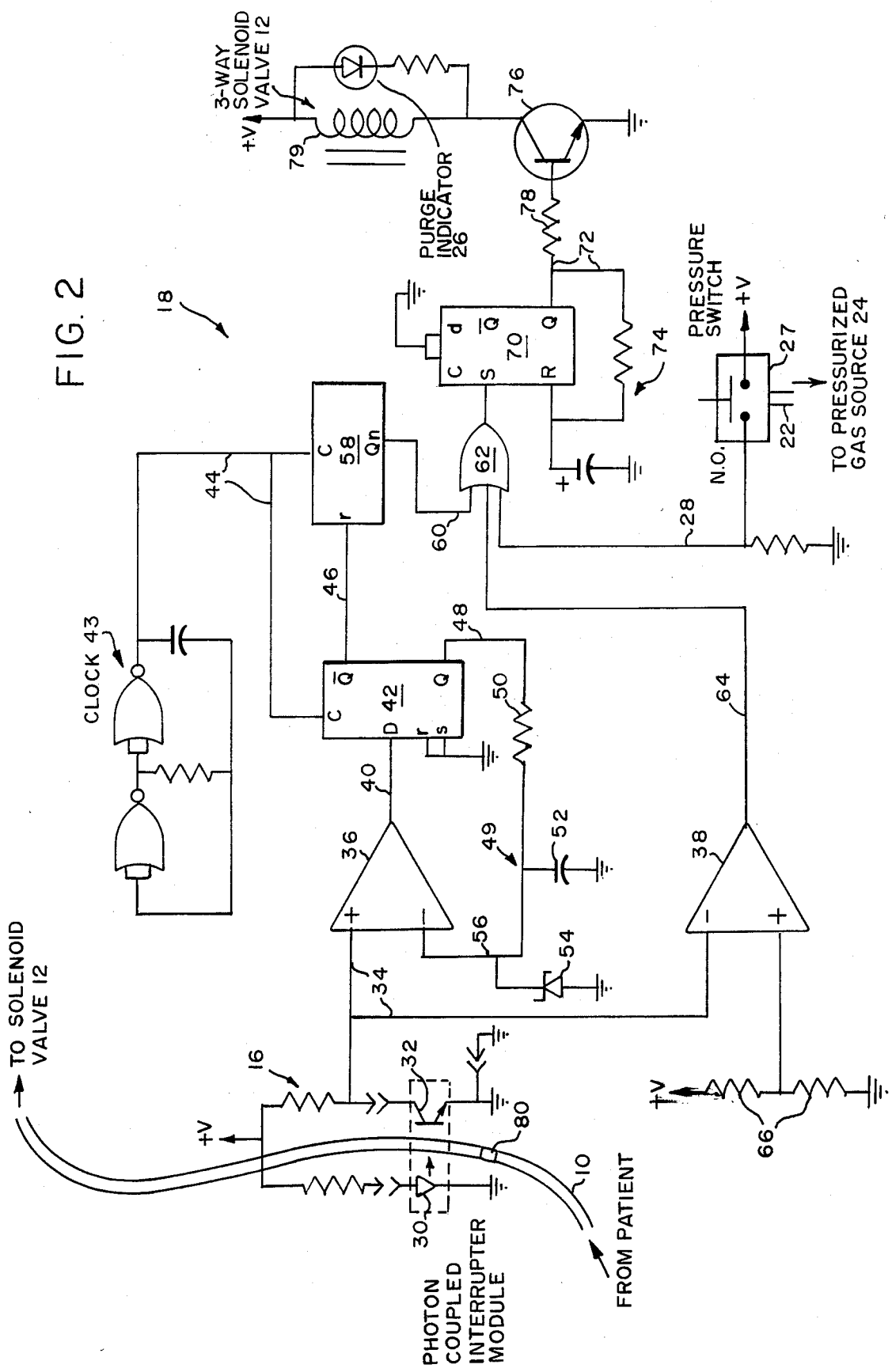

DISCONTINUITY DETECTOR

BACKGROUND OF THE INVENTION

The invention relates to a detector of sudden changes or discontinuities in a medium moving relative to the detector and, more particularly, to such a detector for flowing fluids in medical diagnostic and therapeutic instruments.

It is desirable in many situations to detect a sudden change or discontinuity moving relative to a detector. Such discontinuities include a liquid plug forced along a gas conduit, a gas bubble forced along or rising up a liquid conduit, or a change from one flowing liquid or gas to another. These discontinuities can damage apparatus at the end of the conduit or interfere with the intended use of the fluid in exemplary ways described below for medical diagnostic and therapeutic instruments. A host of other discontinuities can also be desirably detected, however, in other arts such as aerial reconnaisance or character recognition, for example.

Medical diagnostic and therapeutic instruments offer good examples of the problems presented by fluid discontinuities. Mass spectrometers or discrete gas analyzers, for example, are desirable diagnostic tools for patients in intensive care or operating theatres. Samples of the patient's breath are drawn into the instrument through a small, capillary-like tube inserted into one of the patient's breath passages. The samples of the patient's breath are then analyzed in the instrument for carbon dioxide or anesthesia content to help diagnose the patient's condition. The patient's breath passages are moist, however. The capillary tube thus frequently fills with a short plug of liquid drawn into the tube with the gas or condensed in the tube as the gas flows to the instrument. If such liquid reaches the instrument it can damage it or interfere with its operation. This problem is so severe that it has restricted the desired use of such gas diagnostic instruments.

Intra-veinous fluid supplies illustrate the problem of fluid discontinuities in medical therapeutic instruments. They are frequently used to supply liquids to a patient's blood stream. It is well known, however, that a gas bubble entering the blood stream with the fluid can be dangerous and even fatal to the patient. The instruments are therefore carefully designed to prevent bubbles from forming in the fluid supply and to trap any bubbles which do form, but generally are not equipped to stop the flow of fluid to the patient if a bubble should escape into the fluid.

There are many other examples in medical and chemical process instrumentation in which it is desirable to detect a discontinuity in a flowing fluid. The diverse desire for such a detector has prompted prior efforts at making one.

One prior effort for a medical respiratory-gas analyzer is disclosed in U.S. Pat. No. 4,197,858 issued Apr. 15, 1980 to John J. Osborn. In the patent, gas to be analyzed is drawn into a chamber through a tube from a patient's breath passage. The gas is then withdrawn form the top of the chamber for analysis while liquid drawn in with the gas settles to the bottom of the chamber. When the liquid reaches a level where it contacts a pair of probes, it changes the electrical conductivity between the probes to trigger a sensing circuit. The sensing circuit then closes a valve in the gas line to the analyzer to prevent the fluid from entering the analyzer and opens a valve to a gas pressure supply to push the liquid from the chamber back along the tube into the patient.

The chamber poses three problems. First, even though it is small, it necessarily permits some mixing of the gas drawn into the chamber at one instant with gas previously drawn in. The analysis of the gas drawn out of the chamber thus represents a mixture of the patient's present condition with his prior condition. Second, the chamber requires sterilization or replacement before the apparatus can be used again because liquid contaminated by a prior patient would otherwise be pushed back into the next patient. Either sterilization or disposal and replacement of the chamber add to the cost and difficulty of using the device. Third, the chamber is position sensitive. If it is improperly set up on its side, or falls over, the liquid may contact the probes supposed to be at the top of the chamber to trigger the purging-pressure response, but not cover the return path to the patient to be purged by the pressure.

Another prior effort is disclosed in U.S. Pat. No. 3,257,782 issued June 28, 1966 to E. L. Weiss. It avoids the mixing problem of the chamber by using discrete electrically-conducting sections as part of a gas supply line. If liquid bridges insulation between a first pair of the conducting sections, an alarm is triggered by conductivity of the liquid. If the liquid progresses further along the line to bridge a second pair of the conducting sections, the conduction of the liquid closes an outlet value for the gas. This arrangement, however, does not avoid the problem of sterilizing or replacing the conducting sections which would arise if the device were used in many medical instruments such as the described respiratory gas analyzer in which the liquid is forced back into the patient.

SUMMARY OF THE INVENTION

It is therefore an object of the invention to provide an improved discontinuity detector and, more particularly, a fluid discontinuity detector which avoids additional sterilizable or replacable components in medical or like use.

It is a further object of the invention to provide a fluid discontinuity detector for a respiratory gas analyzing system.

To these ends, the invention provides a discontinuity detector which detects a sudden change or discontinuity in a medium moving relative to the detector. In the preferred embodiment, a fluid flows through the detector for detecting a discontinuity in the flowing fluid. In other embodiments, the discontinuity may move past a stationary detector in a stationary medium, as when a bubble rises in a liquid past the detector, or the detector may be moved relative to the medium. In still other embodiments, time may provide the relative motion as when, for example, the detector is used to detect the discontinuity from ambient light to dark.

The detector has a sensor appropriate for sensing the desired discontinuity. In the preferred embodiment, the sensor is a photo-diode, photo-transistor pair positioned on opposite sides of a translucent tube passing the sensor and carrying patient gas in which it is desired to detect liquid-plug discontinuities. The tube is required to obtain the sample of patient gas. The detector thus requires neither a chamber nor other sterilizable or replaceable components for use in medical instruments.

A modulator in the detector periodically resets a clock pulse counter until the sensor signals a discontinuity. The clock pulses then increment the counter to a count higher than it reaches between the normal, periodic resettings by the modulator to detect the discontinuity. The detector thus allows the use of off-the-shelf digital integrated components for easy, low-cost construction. The detector can also be designed to provide any desired time delay in signalling a discontinuity, for example to discriminate against short, spurious signals from the sensor, merely by selecting the higher-than-normal count which the counter must reach to detect the discontinuity in relation to the clock pulse frequency.

The modulator preferably is an analog-to-digital delta modulator. The feedback loop in the delta modulator compensates for gradual changes in a quiescent signal from the sensor. This adapts the detector for long use with photoelectric and like sensors which are prone to aging, temperature and other gradual signal changes which could cumulate over time to a level which would spuriously indicate a discontinuity or similar gradual sensor signal changes caused by gradual changes in the medium in which the discontinuity is to be detected.

The digital component construction of the preferred detector also allows other features to be added to the detector merely with an OR gate at the output from the counter which signals the discontinuity. One preferred feature is a threshold detector which indicates sensor malfunctioning or missassembly when its threshold is violated. Another preferred feature, when the detector is intended for a medical patient gas analyzer which purges fluids from the gas-sampling line back into the patient, is a pressure detector to signal inadequate purging pressure. The signals of both these preferred features can be added through the OR gate.

DESCRIPTION OF THE DRAWINGS

A preferred embodiment which is intended to illustrate and not to limit the invention will now be described with reference to drawings, in which:

FIG. 1 is a schematic of the preferred embodiment of the discontinuity detector for a medical patient gas analyzer;

FIG. 2 is an electrical schematic of the discontinuity detector portion of the embodiment shown in FIG. 1; and FIG. 3 is a schematic of a portion of another embodiment of the discontinuity detector.

DESCRIPTION OF THE PREFERRED EMBODIMENTS

FIG. 1 shows a medical patient gas analyzer. A small, capillary-like tube 10 extends from one of the patient's breath passages (not shown) to a three-way, low-volume solenoid valve 12. The valve normally connects the tube to a mass spectrometer or other discrete gas analyzer 14. A negative pressure in the analyzer then draws a small, sample flow of gas from the patient through tube 10 and valve 12 for analysis. The valve 12 has a low volume, as close to that of the tube as possible, to avoid mixing (consolidating) the sample flow to the analyzer, as occurs in prior sampling chambers, and thus assures a continuously accurate sample flow to the analyzer.

At least a portion of the tube 10 is translucent or transparent; much standard medical tubing is. An infrared photoelectric sensor 16 straddles the translucent portion of the tube to sense any plugs of liquid which may be carried along the tube from the patient or condense in the tube. The infrared light is particularly absorbed by water, so the sensor sends a strong, sudden signal to a detector control circuit 18 upon the appearance of a liquid plug at the sensor.

The detector control circuit 18 responds to the sensor signal with a signal over line 20 to the valve 12. The valve then disconnects the tube 10 from the analyzer 14 so that the plug of liquid cannot enter the analyzer and damage it, and connects the tube 10 to a gas pressure line 22. Pressurized gas from a source 24 then passes through the line and valve into the tube 10 to purge the liquid plug from the tube back into the patient. The tube 10 is of small diameter for patient comfort so that the volume of pressurized gas to purge it and the plug of liquid pushed back into the patient are too small for the patient to notice. The detector control circuit also triggers a purge indicator 26 simultaneously with the purging operation.

A pressure-responsive switch 27 is connected to purging gas line 22. It sends a signal to the detector control circuit 18 over line 28 to hold the detector in the purging mode if the pressure from the source drops below that required to purge the tube 10.

The sensor 16 is sufficiently upstream of the valve 12 relative to the direction and speed of patient gas flow to the analyzer for the value to switch to the purging operation before the liquid plug reaches the valve. Then, since the sensor straddles the tube 10 which is required for sampling the patient gas, no additional components require sterilization or replacement for reuse of the analyzer. Instead, merely the patient gas tube 10 to the valve is changed as it would be in any event before insertion into the breath passage of another patient. In addition, there is no chamber in the patient gas flow path to dilute the gas with that previously sampled. The analyzer 14 thus gives a more immediate and accurate indication of the patient's condition.

FIG. 2 shows the structure of the detector sensor 16 and control circuit 18. The sensor is a forward-biased infrared light-emitting diode 30 and light-responsive phototransistor 32 on opposite sides of the tube 10 straddled by the sensor; it may be, for example, a photon coupled interrupter module H21A4 made by General Electric. Line 34 carries the collector potential of the phototransistor to one input of each of two differential amplifiers 36, 38. These may be sections of an integrated operational amplifier.

The output of differential amplifier 36 is fed over line 40 to the inhibit input D of a flip-flop 42. A clock pulse generator 43 provides clock pulses at, for example, 1.8 kHz over line 44 to another input of flip-flop 42 to cause it to alternate logic level output states between a pair of output lines 46, 48 when there is no signal on line 40. When there is a positive potential at the inhibit input of flip-flop 42 from line 40, the flip-flop holds a logic 1 on line 48 and a logic 0 on line 46, and when there is a negative potential from line 40, it holds the opposite logic states on lines 46, 48.

Line 48 connects to a time-dependent network at 49. The network is composed of a resistor 50, capacitor 52, and Zener diode 54 parallel-connected as an overload drain to ground. The value of the resistor and capacitor is selected to provide slope overload at the clock frequency. That is, the time-dependent network 49 is designed so that the signal through the time-dependent network changes more slowly than the anticipated gradient of the sensor signal on line 34 to make sure the flip-flop is inhibited by the sensor signal long enough to trigger the desired output signal as later described.

The output from the time dependent network 49 is carried over line 56 to another, difference input of the differential amplifier 36 to complete a feedback loop around the amplifier and flip-flop. Amplifier 36, flip-flop 42, and time-dependent network 49 thus form a delta modulator.

Line 46 connects to a reset input of a counter 58 which counts pulses from the clock 43 on line 44. An output port Qn of counter 58 provides a logic 1 to line 60 when the counter has counted more than one clock pulse. The counter 58 may be, for example, an integrated counter designated 4024. It provides a binary count at discrete output ports corresponding to the orders of the digits of the binary pulse-count number. In theory, it would be possible to reset the counter via line 46 before the counter increments in response to a second clock pulse over line 44. In practice, however, it is undesirable to time the circuit so exactingly. Instead, an output port higher than the second order is selected for port Qn to line 60, and the frequency of the clock pulses increased to set the circuit response speed.

The clock, sensor, modulator, and counter components described so far comprise all the components of the basic discontinuity detector. The logic 1 signal on line 60 indicates a discontinuity in the gas flowing in tube 10. The remaining components and features desirable for using the detector in a medical patient gas analyzer. These features are added to the detector response by an OR gate 62.

Line 60 is connected as one input to OR gate 62. An output line 64 from the differential amplifier 38 provides a second input to the OR gate. One, subtractive input to the differential amplifier 38 receives the phototransistor collector potential over line 34 as before described. A second, additive input to the amplifier receives a threshold potential preset by potential-dividing resistors 66.

A third input to OR gate 62 is provided over line 28 from the pressure-responsive switch 27. As indicated, switch 27 is normally open in response to sufficient purging gas pressure in gas line 22 from source 24 (FIG. 1). When there is insufficient purging gas pressure, switch 27 closes to feed a signal over line 28 to the OR gate.

The OR gate 62 responds to high logic signals over any of its input lines 60, 64 and 28 with a signal to the set input port S of another flip-flop 70. Both flip-flops 42 and 70 may be implemented from different sections of an integrated component designated 4013, but in different ways. Flip-flop 42 is arranged to complement outputs until disabled via line 40, a D flip-flop arrangement. Flip-flop 70, however, is arranged to set and hold an output logic 1 on line 72 in response to a signal at its set port S until reset, a set/reset flip-flop arrangement.

Line 72 is connected to a time-dependent resistive-capacitive network at 74. The network feeds back to a reset input R of flip-flop 70 to reset it to a logic 0 on line 72 after the time delay of the network. Flip-flop 70 is thus arranged as a one shot.

Line 72 is also connected to the base of a transistor switch 76 through a resistor 78. The collector current of the transistor switch passes through the coil 79 of the solenoid valve 12 and the purge indicator 26 to operate both in response to the logic 1 potential from line 72.

OPERATION

When the sensor 16 properly straddles the tube 10 and the tube carries the patient gas to the analyzer 14 as desired, some of the infrared light from light-emitting diode 30 is absorbed by the tube and gas to limit the phototransistor collector current and establish a corresponding quiescent collector potential on line 34. The quiescent potential exceeds that set by resistors 66 as the threshold of differential amplifier 38. The amplifier 38 then provides a low level signal over line 64 which does not trigger a response from OR gate 62.

If, however, the tube 10 is improperly positioned in the sensor, more light reaches the phototransistor and its collector potential on line 34 drops below the threshold potential of differential amplifier 38. Similarly, if the sensor is exposed to too much ambient ultraviolet light, the phototransistor collector potential drops. The collector potential would similarly drop if the phototransistor shorts out. In each case, the amplifier 38 then provides a high level signal over line 64 which triggers OR gate 62. Its signal sets flip-flop 70 to a logic 1 on line 72. This causes the transistor 76 to conduct, and its current operates the valve 12, and purging indicator 26, to purge the tube 10 as before described. After the time delay of network 74, reset port R of flip-flop 70 receives the logic 1 from line 72. This, however, has no effect as long as the flip-flop is still receiving the set signal from amplifier 38. The resulting continued purging thus indicates that the tube is improperly positioned in the sensor, that the sensor is exposed to too much ambient light or that the sensor has shorted.

A continued purge indication from indicator 26 can also indicate insufficient purging pressure. If insufficient purging gas pressure in gas line 22 allows switch 27 to close, it provides a triggering signal to OR gate 62. This also sets and holds flip-flop 70 to trigger and hold the purging operation and indication. Other embodiments of the invention may, of course, have separate indicators for these conditions.

Meanwhile, when the detector is first turned on, the quiescent or lower collector potential on line 34 triggers a positive potential response from differential amplifier 36. This holds flip-flop 42 with a logic 1 on line 48 which gradually charges capacitor 52 toward the potential on line 34 over the time response period of network 49. The complementary logic 0 simultaneously held on line 46 from flip-flop 42 to counter 58 does not reset the counter. The counter therefore increments in response to the clock pulses on line 44, and preferably reaches the count necessary to provide a logic 1 over line 60 in the time required to charge capacitor 52 to the quiescent potential normally on line 34. This triggers the OR gate 62 to set flip-flop 70 to switch valve 12 to purge tube 10. The preferred initial response thus is to purge tube 10 to make sure it is free of liquid which could have entered in positioning it in the patient's breath passage. In other arrangements, however, the detector need not respond when turned on merely by selecting a clock pulse count for a response on line 60 which takes longer to reach than the capacitor takes to charge to the quiescent potential.

When capacitor 52 reaches the quiescent potential, line 56 provides it to differential amplifier 36 to cancel the positive output over line 40. Flip-flop 42 is then free to respond to the clock pulses on line 44 with the alternating bit stream of logic 1's and 0's on each of its output lines 46 and 48.

The first logic 1 on line 46 resets the counter 58 to a zero count. This removes the logic 1 form the counter output line 60 to allow flip-flop 70 to reset after the time delay of network 74 to end the initial purging of tube 10. Each succeeding logic 1 in the bit stream on line 46 also resets counter 58. The clock pulse count required in counter 58 to produce its output on line 60 is selected to be higher than the number of clock pulses counted between each of the bit stream logic 1's from flip-flop 42 so that the counter does not again trigger purging until a liquid plug 80 reaches the sensor, as later described.

The difference between the clock pulse count reached between each bit stream logic 1 and the clock pulse count required to trigger the counter output sets a delay time. The delay time is selected in relation to the time constant of network 49 so that capacitor 52 can charge to slightly different potentials. This allows the detector to compensate for aging and other small, gradual variations in the quiescent sensor potential.

When the quiescent sensor potential on line 34 changes slightly, differential amplifier 36 produces an output on line 40 of a polarity corresponding to the change. If the quiescent sensor potential rises slightly, a positive signal on line 40 holds flip-flop 42 with a logic 1 on line 48 to charge capacitor 52 to the slightly higher potential which cancels the output on line 40, as before. This occurs for the small change in the quiescent potential in less time than it takes for the clock pulses to increment the counter to the count required to trigger signal on line 60. The detector compensates in this way small increases in the sensor output without triggering a purging output from the detector.

Similar compensation occurs if the sensor quiescent potential falls slightly. This produces a negative signal on line 40 from the differential amplifier 36 to flip-flop 42 which holds the flip-flop with a logic 0 on line 48. The logic 0 on line 48 drains potential from capacitor 52 until its potential equals the lowered quiescent potential on line 34. This stops the amplifier output signal on line 40 to restart the bit stream form flip-flop 42, as before. Again, too, this is done before the clock pulses increment counter 58 to the count necessary for its purge-triggering output over line 60.

Finally, when the sensor 16 properly straddles the tube 10 and the tube carries a liquid plug 80 to the sensor, the liquid absorbs much more of the infrared light from light-emitting diode 30 than the gas. This establishes a phototransistor collector potential on line 34 which is much higher than the quiescent potential. An aperture (not shown) about 1 mm. in diameter, for example, or other optical devices can limit the light path from the diode to the phototransistor to define correspondingly the size of the plug 80 which changes the potential on line 34 in this way.

The higher, plug-produced potential on line 34 produces a positive output from differential amplifier 36 which holds flip-flop 42 with a logic 1 on line 48, as before. This time, however, the time constant of network 49 prevents capacitor 52 from reaching the much higher potential now on line 34 to restart the bit stream to rest the counter until after the counter increments to the clock pulse count which triggers its purge-producing output over line 60.

ANOTHER PREFERRED EMBODIMENT

FIG. 3 shows a portion of another preferred embodiment which differs from that previously described only in the addition of switch 82. When switch 82 is in the upper position indicated in the Figure, the embodiment is functionally the same as that just described. It detects liquid plugs 80 in tube 10 with a signal over line 60 from counter 58.

When switch 82 is thrown to the lower position, however, counter 58 is connected for reset by logic 1's on line 48, instead of line 46. This simple change by a single switch converts the detector for detecting gas bubbles 80' in a liquid flowing through tube 10.

The liquid now normally in tube 10 absorbs much of the infrared light passing form light-emitting diode 30 to phototransistor 32. This produces a high quiescent potential on line 34 which is matched by a high potential on capacitor 52 after an initial charging interval like that previously described, but longer. No signal is therefore carried over line 40 from the differential amplifier 36 to flip-flop 42. The flip-flop therefore provides an alternating bit stream on line 48 which continually resets counter 58 before it reaches the clock pulse count necessary to provide an output over line 60.

When the gas bubble 80' reaches the sensor, it allows more light to reach the phototransistor. This drops its collector potential on line 34 to produce a negative signal over line 40 to flop-flop 42. This, in turn, holds a logic 0 on line 48 which drains capacitor 52 toward the lowered collector potential on line 34. Before capacitor 52 reaches the potential of line 34, however, counter 58 increments to the clock pulse count necessary to trigger a detector response on line 60.

Detection of a gas bubble in a liquid in this way could close a valve in an intra-veinous liquid-supply tube. A single detector assembly with switch 82 could thus be used for either a medical patient gas diagnostic instrument or a medical intra-veinous therapeutic instrument.

Variations in the preferred embodiments now described and their intended uses to detect liquid discontinuities in a gas or gas discontinuities in a liquid preferably in medical diagnostic or therapeutic instruments as will occur to those in the art are intended to be included within the scope of the invention defined by the following claims.

I claim:
1. A discontinuity detector comprising:
   a. sensor means for response with a sensor signal to a discontinuity in a medium moving relative to the sensor;
   b. a clock pulse generator which generates clock pulses;
   c. modulation means responsive to the clock pulses for providing a periodic signal and responsive to the sensor signal for interrupting the periodic signal; and
   d. a counter incremented by the clock pulses and reset by the periodic signal, whereby a count in the counter higher than that reached in the normal period of the periodic signal indicates a discontinuity.

2. A discontinuity detector as in claim 1, wherein the sensor means also provides a quiescent signal and the modulation means is a delta modulator for compensating for gradual changes in the quiescent sensor signal.

3. A discontinuity detector as in claim 2 wherein the sensor means is adapted to receive a tube carrying a flowing fluid medium in which the discontinuity is to be detected and provides a first quiescent sensor signal when the tube is not received in the sensor means and second quiescent sensor signal when the tube is received, and wherein the delta modulator compensates for the second quiescent sensor signal after the counter indicates a discontinuity when the detector is first turned on.

4. A discontinuity detector as in claim 3, and further comprising: means responsive to the first quiescent sensor signal for indicating that the tube has not been received in the sensor means.

5. A discontinuity detector as in claim 2, wherein the sensor means is adapted to receive a tube carrying a flowing fluid medium in which the discontinuity is to be detected and provides a first quiescent sensor signal when the tube is not received in the sensor means and a second quiescent sensor signal when the tube is received, and further comprising: means responsive to the first quiescent sensor signal for indicating that the tube has not been received in the sensor means.

6. A discontinuity detector as in claim 1, wherein the modulation means has a differential amplifier having a pair of differential inputs one of which receives the sensor signal and an output which provides a signal which is the difference of the potentials at the inputs, a flip-flop responsive to the clock pulses with alternate logic states at a pair of outputs a first one of which is connected to the counter to provide with the alternate logic states the periodic signal for resetting the counter, and a time-dependent feedback potential network connecting the second of the flip-flop outputs to the other differential input of the differential amplifier, the output of the differential amplifier being connected to the flip-flop to disable it from alternating logic states at its outputs with the logic state held on the outputs determined by the polarity of the difference signal from the output of the differential amplifier such that the potential of the feedback network changes toward the potential of the sensor signal.

7. A discontinuity detector as in claim 6, and further comprising switch means for switching the connection of the flip-flop to the counter from the first to the second of the flip-flop outputs.

8. A discontinuity detector as in claim 7, wherein the sensor means is adapted to receive a tube carrying a flowing fluid medium in which the discontinuity is to be detected and provides a first quiescent sensor signal when the tube is not received in the sensor means and a second quiescent sensor signal when the tube is received, and further comprising: means responsive to the first quiescent sensor signal for indicating that the tube has not been received in the sensor means.

9. A discontinuity detector as in claim 6, wherein the sensor means is adapted to receive a tube carrying a flowing fluid medium in which the discontinuity is to be detected and provides a first quiescent sensor signal when the tube is not received in the sensor means and a second quiescent sensor signal when the tube is received, and further comprising: means responsive to the first quiescent sensor signal for indicating that the tube has not been received in the sensor means.

10. A discontinuity detector as in claim 1, wherein the sensor means is adapted to receive a tube carrying a flowing fluid medium in which the discontinuity is to be detected and provides a first quiescent sensor signal when the tube is not received in the sensor means and a second quiescent sensor signal when the tube is received, and further comprising: means responsive to the first quiescent sensor signal for indicating that the tube has not been received in the sensor means.

11. In a medical instrument having a tube carrying a flowing fluid, a discontinuity detector for signaling a discontinuity in the fluid, and a valve connected to the tube and responsive to the discontinuity signal from the detector for cutting-off the fluid flow in the tube, an improved discontinuity detector comprising:
  a. sensor means juxtaposed the tube for response to a discontinuity in the fluid flowing in the tube with a sensor signal having a quiescent level when no discontinuity is detected;
  b. a clock pulse generator which generates clock pulses;
  c. delta modulation means responsive to the clock pulses for providing a periodic signal, responsive to the sensor signal for interrupting the periodic signal, and responsive to the quiescent level of the sensor signal for compensating for gradual changes in the quiescent sensor signal; and
  d. a counter incremented by the clock pulses and reset by the period signal which provides a discontinuity signal when the counter reaches a selected clock pulse counter higher than that reached in the normal period of the periodic signal.

12. In a medical instrument as in claim 11, wherein the sensor means provides another quiescent signal when the tube improperly passes the sensor means, and further comprising: means responsive to the other quiescent signal for indicating that the tube improperly passes the sensor means.

13. In a medical instrument as in claim 12, wherein the valve connects the tube to a source of pressurized purging fluid when it cuts-off the fluid flow in the tube, and further comprising: pressure-responsive switch means responsive to inadequate purging pressure from the source for holding the valve in the condition cutting-off the fluid flow in the tube.

14. In a medical instrument as in claim 11, wherein the valve connects the tube to a source of pressurized purging fluid when it cuts-off the fluid flow in the tube, and further comprising: pressure-responsive switch means responsive to inadequate purging pressure from the source for holding the valve in the condition cutting-off the fluid flow in the tube.

* * * * *